(12) United States Patent
Escaned-Barbosa et al.

(10) Patent No.: US 12,593,988 B2
(45) Date of Patent: Apr. 7, 2026

(54) METHOD AND DEVICE FOR DETERMINING A CORONARY MICROVASCULAR RESISTANCE SCORE

(71) Applicant: Medis Associated B.V., Leiden (NL)

(72) Inventors: Javier Escaned-Barbosa, Madrid (ES); Hernán David Mejía Rentería, Madrid (ES); Johan Hendrikus Christiaan Reiber, Rotterdam (NL)

(73) Assignee: QFR Solutions B.V., Leiden (NL)

( * ) Notice: Subject to any disclaimer, the term of this patent is extended or adjusted under 35 U.S.C. 154(b) by 608 days.

(21) Appl. No.: 18/017,706

(22) PCT Filed: Jul. 23, 2021

(86) PCT No.: PCT/NL2021/050470
§ 371 (c)(1),
(2) Date: Jan. 24, 2023

(87) PCT Pub. No.: WO2022/019765
PCT Pub. Date: Jan. 27, 2022

(65) Prior Publication Data
US 2023/0263401 A1 Aug. 24, 2023

(30) Foreign Application Priority Data
Jul. 24, 2020 (NL) ..................................... 2026137

(51) Int. Cl.
*A61B 5/02* (2006.01)
*A61B 5/021* (2006.01)
*A61B 5/026* (2006.01)

(52) U.S. Cl.
CPC .......... *A61B 5/02007* (2013.01); *A61B 5/021* (2013.01); *A61B 5/026* (2013.01)

(58) Field of Classification Search
CPC ..... A61B 5/02007; A61B 5/021; A61B 5/026; A61B 5/0044; A61B 5/0215; A61B 5/7278; A61B 5/1076; G16H 30/40; G16H 50/50
See application file for complete search history.

(56) References Cited

U.S. PATENT DOCUMENTS

2013/0246034 A1 9/2013 Sharma et al.
2015/0051888 A1 2/2015 Itu et al.
(Continued)

FOREIGN PATENT DOCUMENTS

CN 201861883 U 6/2011
EP 3660858 A1 6/2020
(Continued)

OTHER PUBLICATIONS

Gibson et al, "TIMI Frame Count: A Quantitative Method of Assessing Coronary Artery Flow", Circulation, vol. 93, Issue 5, Mar. 1, 1996; pp. 879-888 https ://www.ahajournals.org/doi/epub/10 .1161/01. CI R.93 .5 .879.
(Continued)

*Primary Examiner* — Eric F Winakur
*Assistant Examiner* — Sienna C Pyle
(74) *Attorney, Agent, or Firm* — Banner & Witcoff, Ltd.

(57) ABSTRACT

A method of determining a microvascular resistance score indicating perfusion of myocardial tissue in a body of a mammal is provided, comprising obtaining acquired blood pressure data and flow data of blood in a cardiac vessel while the mammal is in a first physiological state; obtaining throughflow data indicative of a geometry the cardiac vessel; generating adjusted blood pressure data and adjusted flow data corresponding to a second physiological state, based on the acquired blood pressure value and the first physiological state; generating the microvascular resistance score, based
(Continued)

on the adjusted blood pressure data, the adjusted flow data and the throughflow data; and providing, through an electronic output signal, the microvascular resistance score for display on an electronic display module.

15 Claims, 2 Drawing Sheets

(56)                  References Cited

U.S. PATENT DOCUMENTS

| | | | |
|---|---|---|---|
| 2017/0032097 A1 | 2/2017 | Itu et al. | |
| 2019/0000559 A1 | 1/2019 | Berman et al. | |
| 2019/0355118 A1* | 11/2019 | Zilberstien | A61B 6/5217 |
| 2019/0365247 A1 | 12/2019 | Veszelei et al. | |
| 2021/0244293 A1* | 8/2021 | Belleville | G16H 50/30 |

FOREIGN PATENT DOCUMENTS

| | | |
|---|---|---|
| JP | 3184531 B2 | 7/2001 |
| JP | 2016528969 A | 9/2016 |
| JP | 2018061883 A | 4/2018 |

OTHER PUBLICATIONS

International Search Report and Written Opinion—PCT/NL2021/050470—mailing date Jan. 27, 2022.

* cited by examiner

202

204

206

208

210

212

232

234

214

216

218

220

222

224

200        226

METHOD AND DEVICE FOR DETERMINING A CORONARY MICROVASCULAR RESISTANCE SCORE

CROSS-REFERENCE TO RELATED APPLICATIONS

This application is a U.S. National Stage application under 35 U.S.C. § 371 of International Application PCT/NL2021/050470 (published as WO 2022/019765 A1), filed Jul. 23, 2021 which claims the benefit of priority to Application NL 2026137, filed Jul. 24, 2020. Benefit of the filing date of these prior applications is hereby claimed. Each of these prior applications is hereby incorporated by reference in its entirety.

TECHNICAL FIELD

The various aspects and implementations thereof relate to an electronic device arranged to compute a coronary microvascular resistance score and a method that may be executed by such devices.

BACKGROUND

For characterising pressure drops in coronary arteries due to narrowings in the vessels, the fractional flow reserve has been defined and generally accepted among the cardiological community. This physiological index may be determined by means of invasive pressure measurements, in the coronary artery under scrutiny. And it may also be determined in a non-invasive way using a reconstruction of the artery under scrutiny, based on images acquired by means of, for example, CT or X-ray imaging protocols, combined with advanced mathematical algorithms. The fractional flow reserve provides an assessment of the functional severity of the narrowings in the artery and in that way, a measure of decreased perfusion of subtended myocardial tissue fed by the coronary artery under scrutiny.

During further research, cases were discovered with decreased perfusion of the myocardial tissue not explained by fractional flow reserve index (i.e. non-ischemic fractional flow reserve value). Investigating causes of abnormal myocardial tissue perfusion beyond coronary artery narrowing requires assessment of other components of the heart circulation, such as the status of the coronary microcirculation, which is constituted of arterioles and capillaries. In this regard, the hyperaemic Index of coronary Microcirculatory Resistance—IMR—was developed several years ago. By combining intracoronary measurements of pressure and flow, the IMR provides an assessment of the minimal microvascular resistance under maximal hyperaemia, ultimately mirroring the capacity of arterioles and capillaries in delivering blood flow to the subtended myocardial tissue under maximal myocardial demands; IMR is defined as the mean distal coronary pressure multiplied by the mean coronary transit time, under hyperaemic conditions. As such, IMR can be consider a metric of vascular resistance at the level of the microcirculation, capable of reflecting an abnormal status of the microvascular network causing impaired myocardial perfusion.

SUMMARY

Assessment of the minimal coronary microvascular resistance requires maximal hyperaemia, a status under which the arterioles and capillaries are completely vasodilated, therefore the vascular resistance is minimal and the coronary flow is maximum. Customarily, potent vasodilator drugs like adenosine are used to bring a body and the heart into a hyperaemic state; however, the use of adenosine and other vasodilator drugs with a similar or equivalent effect is not always preferred or even possible. As IMR is defined as an index or score acquired or to be acquired in hyperaemic state of a body, limitations are encountered in the real practice to use this invasive physiological index. Development of other methods aimed to assess the coronary microcirculation not requiring the use of vasodilator drugs to induce hyperaemia nor coronary instrumentation with dedicated wires is desirable.

A first aspect provides, in an electronic computing device, a method of determining a coronary microvascular resistance score indicating vascular resistance of coronary microcirculation in a body of a mammal and a human in particular. The method comprises receiving data on blood pressure of a cardiac vessel supplying blood to the myocardial tissue acquired while the mammal is in a first physiological state, preferably data at a proximal location of a coronary artery, receiving data on flow velocity of blood in the cardiac vessel acquired while the mammal is in a first physiological state and receiving obtaining throughflow data like, for example, a fractional flow reserve, indicative of the pressure drops in the cardiac vessel, as well as the geometry of the cardiac vessel. The method further comprises generating adjusted blood pressure data corresponding to a second physiological state, based on the acquired blood pressure value at the first physiological state and generating adjusted flow data corresponding to a second physiological state, based on the acquired flow data at the first physiological state. Based on the adjusted blood pressure data, the adjusted flow data and the throughflow data, the coronary microvascular resistance score is generated and provided, through an electronic output signal, for display on an electronic display module.

By transforming received data values obtained from the object under scrutiny in the first physiological state, for example a rest state, to adjusted data corresponding to the second physiological state, it is possible to determine the IMR or similar scores, without a requirement for bringing the object under scrutiny to the second physiological state for obtaining the parameters. A proximal end of a vessel is to be understood as an upstream end of the vessel and a distal end of the vessel is to be understood as a downstream end of a vessel, relative to the displacement of blood through the vessel.

In an implementation, generating adjusted blood pressure data comprises retrieving a mapping relation between first blood pressure data in the first physiological state and second blood pressure data in the second physiological state. This implementation provides an efficient way to provide adjusted values.

In a further implementation, the relation is described by at least one of a table and a curve. With a table comprising multiple data points, a particular accuracy may be achieved with a low computing requirement. With a curve, in particular when described by means of an analytical rather than numerical relation, a very accurate transformation may be applied, resulting in accurate adjusted data.

In another implementation, generating adjusted flow data comprises retrieving a mapping relation between first flow data in the first physiological state and second flow data in the second physiological state. This implementation provides an efficient way to provide adjusted values.

In yet a further implementation, the relation is described by at least one of a table and a curve. With a curve, in particular when described by means of an analytical rather than numerical relation, a very accurate transformation may be applied, resulting in accurate adjusted data.

In again another implementation, the first physiological state is a non-hyperaemic state and the second physiological state is a hyperaemic state. This implementation is particularly practical for determining the IMR.

A second aspect provides a data processing apparatus/device/system comprising a processor configured to perform the method of the first aspect or implementations thereof.

A third aspect provides a computer program product comprising instructions which, when the program is executed by a computer, cause the computer to carry out the method of the first aspect.

A fourth aspect provides a non-transitory computer readable medium comprising instructions which, when executed by a computer, cause the computer to carry out the method of the first aspect.

A fifth aspect provides, independently from the first aspect, in an electronic computing device, a method of determining a microvascular resistance score indicating perfusion of myocardial tissue in a body of a mammal. The method comprises obtaining a value for blood pressure of a cardiac vessel at a proximal end of the cardiac vessel, the cardiac vessel supplying blood to the myocardial tissue acquired by monitoring the mammal while the mammal is in a non-hyperaemic state, obtaining at least one of an acquired transit time and an acquired blood flow rate of blood in the cardiac vessel acquired by monitoring the mammal while the mammal is in the non-hyperaemic state and obtaining the fractional flow reserve of the cardiac vessel at a distal end of the cardiac vessel. The method further comprises generating an adjusted blood pressure corresponding to a hyperaemic state, based on the acquired blood pressure value and the first physiological state and generating at least one of an adjusted acquired transit time and an adjusted acquired flow rate of blood corresponding to a hyperaemic state, based on the acquired transit time and an acquired blood flow rate of blood in the cardiac vessel. The method also comprises generating the microvascular resistance score by at least one of multiplying the fractional flow reserve at a distal end of the cardiac vessel, an adjusted blood pressure data and the adjusted transit time and multiplying the fractional flow reserve at a distal end of the cardiac vessel, an adjusted blood pressure data and the inverse of the adjusted blood flow rate and providing, through an electronic output signal, the microvascular resistance score for display on an electronic display module. This aspect may be implemented in a device and a computer program product.

BRIEF DESCRIPTION OF THE DRAWINGS

The various aspects and embodiments thereof will now be discussed in conjunction with drawings. In the figures.

DETAILED DESCRIPTION

Figure 1:
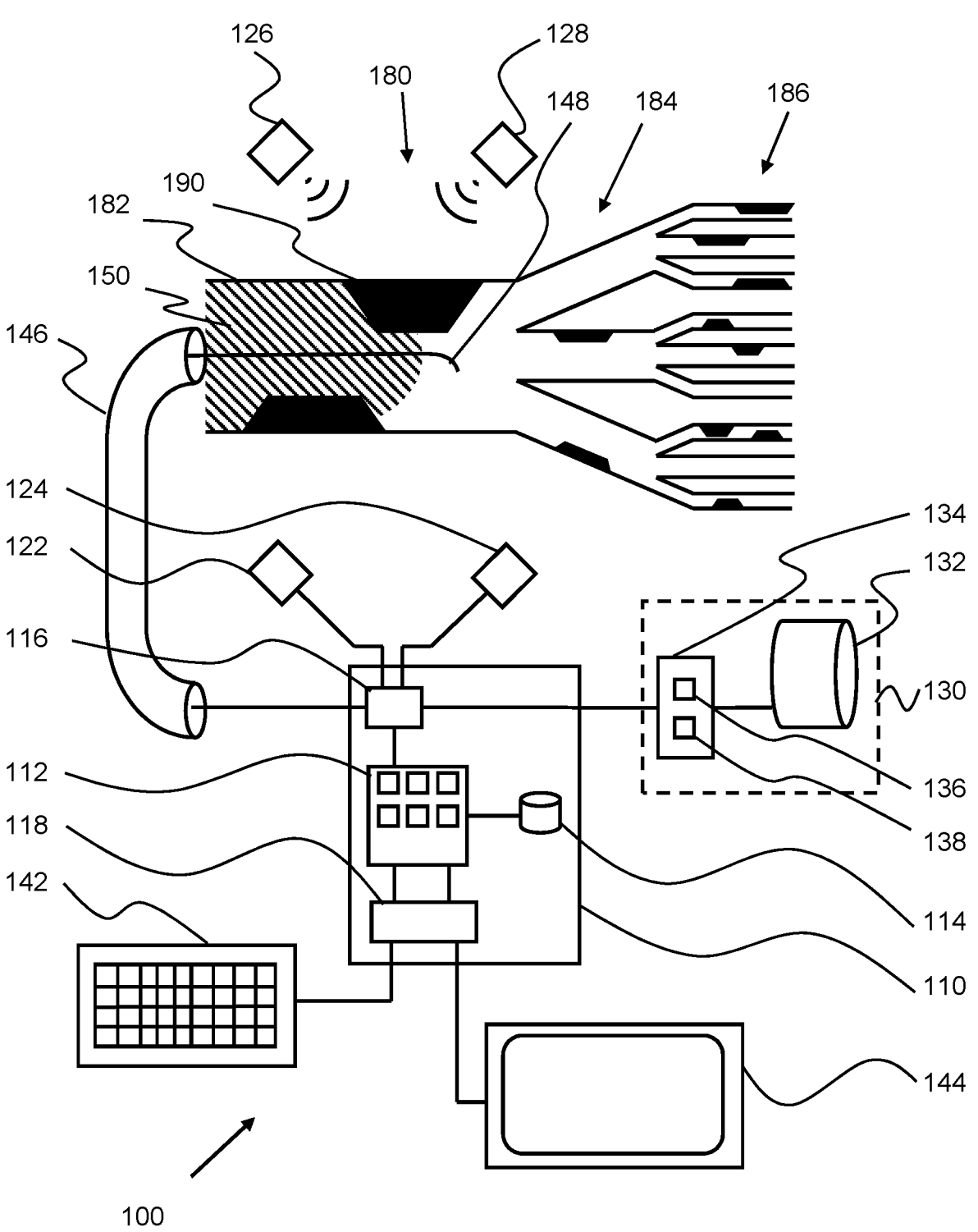
FIG. 1: shows an electronic medical data acquisition and processing system.

FIG. 1 shows an electronic medical data acquisition and processing system 100 as an example of the second aspect. The system 100 or at parts thereof may be found in a cardiac catheterisation laboratory of a clinic or a hospital. The system 100 comprises an X-ray image acquisition module comprising a first X-ray source 126 and a second X-ray source 128, a first X-ray detector 122 arranged to receive X-ray data from the first X-ray source 126 and a second X-ray sensor 124 arranged to receive X-ray data from the second X-ray source 128.

The first X-ray detector 122 and the second X-ray detector 124 are connected to data acquisition module 116 of an electronic computing device 110. The electronic computing device further comprises a processing unit 112, a storage module 114 and a peripherals I/O controller 118. The processing unit 112, which may be implemented as a microprocessor, microcontroller or other electronic data processing device, is arranged to control the various part of the electronic computing device 110 and the system 100 and arranged to execute the method according to the first aspect and implementations thereof.

The storage module 114 is arranged for storing data thereon, for example acquired by the computing device 110 from the various other parts of the system 100, either directly or after processing by the processing unit 112. The storage unit 114, as at least partially implemented as a non-transitional storage medium, is further arranged for storing computer executable code which allow the processing unit 112 to execute the method according to the first aspect and implementations thereof.

The system 100 further comprises, in this implementation as an option, a first blood pressure measurement module 130 comprising a pressure cuff 132 and a control unit 134 comprising a pulse sensor 136 and a pressure control unit 138 arranged to control air pressure in the pressure cuff 132 by inflating and deflating the pressure cuff 132.

The system 100 comprises a pressure tip 148 as a another blood pressure measurement module, which corresponds to the intracoronary distal pressure. The pressure tip 148, which is connected to a coronary wire, transmits the pressure to the data acquisition module 116, from a coronary artery 182 of a cardiovascular structure 180 as an example of a coronary vessel or blood vessel in general via a catheter 146 inserted in a body of a mammal, like a human being. Additionally, the tip of the coronary catheter 146, placed into the ostium of the coronary artery under scrutiny 182, sense the proximal pressure into the vessel, which corresponds to the aortic pressure. The cardiovascular structure 180 shown by FIG. 1 may be a hypothetical structure and is not necessarily a representation of an actual anatomical structure.

The peripherals I/O controller 118 is arranged to connect the computing device 110 and the various components thereof to input device like a keyboard 142 or a touch screen for receiving data like user input. The peripherals I/O controller 118 is arranged to connect the computing device 110 and the various components thereof to output devices like an electronic display 144 and other output devices arranged to provide a user with data on processed or unprocessed data received by the computing device 110.

As shown in FIG. 1, the catheter 146 and the pressure wire 148 are inserted in the coronary artery 182. To the right, the coronary artery 182 develops further in a microvascular structure 184 and 186. In the main artery, narrowings 190 are present. The stenotic areas result in narrowing in the various vessels of the coronary vascular structure 180, which, in turn results in pressure drops at the various stenotic areas. Subsequently, the pressure drops result in reduced perfusion of myocardial tissues, which leads to reduced physical condition of the person under scrutiny.

Figure 2:
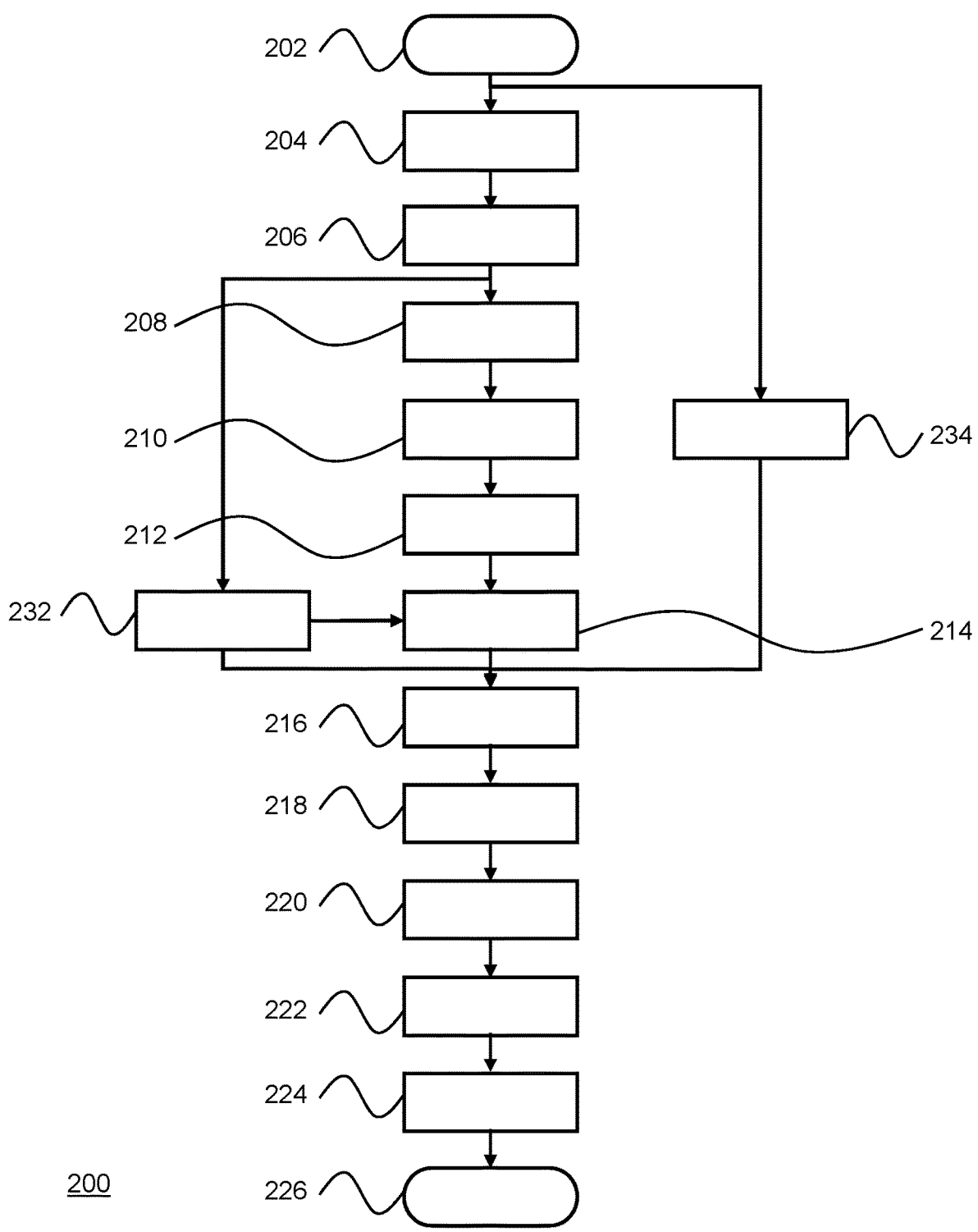
FIG. 2: shows a flowchart depicting an example of the first aspect.

The further functionality of the system 100 and parts thereof discussed above will be further elucidated in conjunction with a flowchart 200 depicted by FIG. 2. The various parts of the flowchart 200 are briefly summarised below.

202 start
    204 acquire first X-ray image set
    206 acquire second X-ray image set
    208 select image from first set
    210 select image from second set
    212 construct model
    214 determine FFR
    216 obtain adjustment data
    218 adjust flow velocity
    220 adjust pressure
    222 calculate IMR
    218
    224 Provide IMR for display
    226 end
    232 determine flow velocity
    234 acquire pressure data The process starts in a first terminator 202 and continues to step 204 in which a first X-ray image set of the coronary artery 182 and is acquired using the X-ray image acquisition module and the first X-ray source 126 and the second X-ray detector 124 in particular, preferably under non-hyperaemic conditions, more preferably in resting condition. To that end, contrast dye 150 is inserted in the coronary artery 182 using the catheter 146. Multiple images, consecutive in time, of the coronary artery 182 are acquired, while the contrast dye 150 progresses in the coronary artery 182. The data is preferably acquired while the person under scrutiny is in a non-hyperaemic state and more preferably while the person is in rest, preferably awake.

Subsequently or in parallel, in step 206, a second X-ray image set of the coronary artery is acquired using the second X-ray source 128 and the first X-ray detector 122. The second X-ray image set is acquired under an angle relative to the way the first X-ray image as has been acquired, preferably at an angle between 20° and 45° and preferably between 30° and 40°.

In parallel, from either the first X-ray image set or the second X-ray image set, a flow velocity of the contrast dye 150 in the coronary artery 182 is determined. With an amount of frames known required for the contrast dye 150 to flow over a particular distance and frame rate or with time known for the contrast dye 150 flow over a particular distance, a flow rate in distance unit per time unit may be acquired, preferably under non-hyperaemic conditions, more preferably in rest condition. Multiplication by a unit for cross-section of the coronary artery 182, a volumetric flow rate may be determined. It is noted that the flow velocity of blood in the coronary artery may also be acquired in other ways, either from data acquired during image data acquisition or based on other data, preferably under non-hyperaemic conditions, more preferably in rest condition.

From the first X-ray image set, a first image is selected in step 208 and in step 210, a second image is selected from the second X-ray image data set, for example in accordance with methods as described by patent application EP 19212979.9, or other methods.

Using the images selected, a geometric model of the vessel or vessels under scrutiny is constructed in step 212. Using the model thus acquired, together with the determined flow velocity, the fractional flow reserve is obtained, preferably calculated, in step 214 as an example of throughflow data related to the artery 182.

Whereas in the example above, the three-dimensional model of a vessel is determined using data acquisition using multiple X-ray sources and detectors is discussed, also other data acquisition method may be used, including, but not limited to optical coherence tomography (OCT), intravenous ultrasound (IVUS), a single X-ray source and detector, optionally to consecutively acquire two sets of images, a single set of images or just single images, computer tomography scans (CT scanning) using contrast dye, other, or a combination thereof.

In parallel to reconstruction of the geometric model of the anatomy of the vessel or vessels, a blood flow velocity may be determined in step 232, based on the first X-ray image set, the second X-ray image set or both image sets. The flow velocity may be determined as described in "TIMI Frame Count" by C. Michael Gibson e.a. as published in Circulation 1996; 93: 879-888 Using the imaging technique applied, preferably X-ray, it is determined, preferably by the processing unit 110, over how much frames contrast dye and in particular a front of a volume thereof flows from a proximal point of a vessel to a point of interest in the vessel, for example a bifurcation or another distal point. Detection of a front of the contrast dye volume may be executed using image recognition, executed by the processing unit 110.

With further information like vessel length and framerate, the flow rate of the contrast dye and thus of blood in the vessel may be determined. It is noted that also other methods of determining the blood flow velocity are available, including obtaining time required for a front of the contrast dye volume to travel from a proximal point to a distal point and a length of the vessel.

Subsequently, the FFR—the fractional flow reserve—may be calculated based on the model or other geometric data thus acquired and/or constructed based on the acquired data and the flow velocity determined in step 232 or obtained otherwise; similar principles will also apply to bifurcation cases, in which the effect of the bifurcation of the calculations of the pressure drops in the individual vessels can be incorporated. The FFR may be calculated using computational fluid dynamics or other analytical or computational models like Quantitative Flow Ratio (QFR). In yet another alternative, the FFR is calculated based on directly acquired pressure values in the artery 182, using the pressure tip 148.

Parallel to or prior to determining the fractional flow reserve, blood pressure of the person is acquired in step 234. Preferably, this is the pressure at a proximal end of the coronary artery 182 obtained with the tip of the coronary catheter 146 preferably under non-hyperaemic conditions, more preferably in resting condition. Usually, this is equal to or very close to the aortic pressure. This blood pressure may be acquired in multiple ways, including, but not limited to using the pressure tip 148 inserted in the coronary artery 182 or available in the aorta of the person under scrutiny. As such, a value of the aortic pressure—systolic, diastolic, an average thereof or otherwise determined based on measured values—may be obtained and used as an assumed pressure of the proximal blood pressure in the applicable cardiac vessel.

Alternatively, or additionally, the first blood pressure measurement module 130 is used to acquire the blood pressure on the arm of the person under scrutiny in a non-invasive way. The pressure value acquired, either maximum (systolic), average of maxima, average, minimum (diastolic), average of minima, with or without further statistical processing, may also be acquired, either via the data acquisition module 116 or the keyboard 142.

Physiological indices of coronary microvascular resistance like IMR are obtained under hyperaemic state which require the use of hyperaemic drugs like adenosine and need the use of a dedicated intracoronary physiology wire. These latter tools of IMR (the wire and the drug) are not always available or may be inappropriate in particular cases. On the other hand, the non-hyperaemic state may be a rest state, either awake or sleep, meaning the opposed state to other heart stress conditions like a state of high activity, sports, just walking, other, or a combination thereof. To calculate IMR without the need of intracoronary physiology wire and hyperaemic drugs like adenosine, estimations of hyperaemic physiology parameters (i.e. coronary pressure and flow) are derived from the resting conditions.

In step 216, adjustment data for adjusting acquired non-hyperaemic data is obtained. Such data may be stored in the storage module 114 and retrieved using the processing unit 112. Such data may be a set of two single values, one for the pressure data and one for the velocity data, a curve or a set of curves, one, two or more formulae, one, two or more curves, one, two or more tables, other data, or a combination thereof.

In one particular implementation, the pressure is adjusted using the following equation, wherein $P_{a,acq}$ is an acquired pressure value and $P_{a,adjusted}$ is an adjusted—estimated hyperaemic—pressure value at a proximal end of the vessel under scrutiny. Blood flow velocity data may be adjusted in a similar way.

$$P_{a,adjusted} = P_{a,acq} - \frac{(P_{a,acq} \times 10)}{100}$$

In case the adjustment data comprises more complex data, like curves and/or tables, the acquired proximal pressure value is mapped or otherwise transformed to an adjusted proximal pressure value, optionally using interpolation or other numerical, statistical and/or analytical operations.

In step 218, the obtained blood flow velocity value or blood flow velocity data is adjusted using the obtained adjustment data. The obtained blood flow velocity data, blood flow velocity value, mean transit time of fluid through a vessel or other indication of acquired blood flow velocity indicator may be adjusted in a way similar to the way the acquired blood pressure is adjusted, as discussed above to the $2^{nd}$ physiologic state (i.e. hyperaemic status) from the QFR algorithm. In one implementation, the adjusted blood flow velocity may be used for determining the FFR in step 214. In such implementation, step 214 is preceded by step 216 and step 218. Once the flow velocity is adjusted to hyperaemic conditions, the coronary mean transit time is derived from the ratio between the length of the vessel segment under scrutiny and the adjusted flow velocity. The FFR may be determined at multiple locations in the coronary artery and in particular at a distal end of the coronary artery.

In step 220, the blood pressure value or the blood pressure data is adjusted using the adjustment data. In step 222, based on the adjusted data, the IMR is calculated using the fractional flow reserve, the adjusted hyperaemic coronary mean transit time and the adjusted aortic pressure. In one particular implementation, the IMR is calculated using the equation directly below, in which FFR is the earlier calculated FFR, which may in this implementation be at a distal point of the applicable coronary artery—in another implementation, it may be at a proximal end, either using models or actually obtained physical pressures in vessels, $P_{a,adjusted}$ is the adjusted aortic or proximal vessel pressure, and $l/v_{adjusted}$ is the adjusted coronary mean transit time, where l is the length of the coronary artery to a point of interest like an entry of vessels into myocardial tissue and $v_{adjusted}$ is adjusted blood flow velocity data:

$$IMR = (FFR \times P_{a,adjusted}) \times \left(\frac{l}{v_{adjusted}}\right)$$

The IMR may be calculated using equations different from the equation directly above, directly using acquired data and incorporating adjustment data, directly using a number of time frames required for contrast dye 150 to arrive at a point of interest in a vessel, vessel length and frame rate, other data, or a combination thereof.

Values may be adjusted to transpose datasets from one domain to another, for example from the hyperaemic domain to the non-hyperaemic domain. Such adjustment step may include a correction step, in which values may be corrected for any reason. Alternatively or additionally, correction may take place separately. Such reason may a correction for environmental factors that may influence data acquisition or values of parameters themselves in a body, a correction for particular equipment used, other or a combination thereof.

In step 224, the IMR as perfusion score or (micro-) vascular resistance score indicating perfusion of the cardiovascular structure 180—or lack thereof—taking into account stenosis 190 in the coronary artery and abnormalities in the microvascular structure 186 as well is further processed by the processing unit 112 for display of the value on the electronic display 144. Alternatively or additionally, data may be prepared to be sent to another data computing structure for display, storage or further processing using a network connection. Subsequently, the process depicted by the flowchart 200 ends in terminator 226.

The invention claimed is:

1. A method of determining a microvascular resistance score, the method comprising:

obtaining acquired blood pressure data of a cardiac vessel supplying blood to myocardial tissue of a mammal, said acquired blood pressure data being acquired while the mammal is in a first physiological state;

obtaining acquired flow data of the blood in the cardiac vessel, said acquired flow data being acquired while the mammal is in the first physiological state;

obtaining throughflow data indicative of a geometry of the cardiac vessel, said throughflow data being acquired by:

measuring a length of the cardiac vessel from a proximal point to a distal point, measuring a transit time of the blood from the proximal point to the distal point, and dividing the length by the transit time to calculate the throughflow data;

generating adjusted blood pressure data corresponding to a second physiological state, based on the acquired blood pressure data and the first physiological state;

generating adjusted flow data corresponding to the second physiological state, based on the acquired flow data and the first physiological state;

generating the microvascular resistance score, based on the adjusted blood pressure data, the adjusted flow data and the throughflow data; and providing, through an electronic output signal, the microvascular resistance score for display on a display module of an electronic computing device, for a user of the electronic computing device to evaluate perfusion of the myocardial tissue.

2. The method according to claim 1, wherein generating adjusted blood pressure data comprises using a blood pressure mapping relation between said acquired blood pressure data in the first physiological state and said adjusted blood pressure data in the second physiological state.

3. The method according to claim 2, wherein the blood pressure mapping relation is described by at least one of a table and a curve.

4. The method according to claim 1, wherein generating adjusted flow data comprises using a flow mapping relation between said acquired flow data in the first physiological state and said adjusted flow data in the second physiological state.

5. The method according to claim 4, wherein the flow mapping relation is described by at least one of a table and a curve.

6. The method according to claim 1, wherein the first physiological state is a non-hyperaemic state and the second physiological state is a hyperaemic state.

7. The method according to claim 1, wherein the blood pressure data comprises at least one of a systolic pressure, a diastolic pressure, an average of the systolic pressure over time, an average of the diastolic pressure over time or an average blood pressure over time.

8. The method according to claim 1, wherein obtaining the acquired flow data comprises:

obtaining a series of images acquired consecutively in time;

determining a first image at which a fluid portion is at the proximal point of the cardiac vessel;

determining a second image at which the fluid portion is at the distal point of the cardiac vessel;

determining a number of images between the first image and the second image;

obtaining a frame rate of images acquired per second;

calculating the flow data by dividing the number of images by the frame rate.

9. The method according to claim 1, wherein the throughflow data is indicative of a fractional flow reserve of the cardiac vessel.

10. The method according to claim 9, wherein the throughflow data is obtained based on a geometrical model of the cardiac vessel and the flow data.

11. The method according to claim 1, wherein the microvascular resistance score is an Index of Microcirculatory Resistance, IMR.

12. The method according to claim 11, wherein the throughflow data is indicative of a fractional flow reserve of the cardiac vessel; and the IMR is obtained by multiplying the fractional flow reserve at the distal end of the cardiac vessel, the adjusted blood pressure data and an adjusted transit time, wherein the acquired flow data comprises a blood flow rate and the adjusted transit time is obtained by dividing the adjusted flow data by the length of the cardiac vessel.

13. A data processing device comprising:

an input configured to:

obtain acquired blood pressure data of a cardiac vessel supplying blood to myocardial tissue of a mammal, said acquired blood pressure data being acquired while the mammal is in a first physiological state;

obtain acquired flow data of the blood in the cardiac vessel, said acquired flow data being acquired while the mammal is in the first physiological state;

obtain throughflow data indicative of a geometry of the cardiac vessel, said flowthrough data being acquired by:

measuring a length of the cardiac vessel from a proximal point to a distal point, measuring a transit time of the blood from the proximal point to the distal point, and dividing the length by the transit time to calculate the throughflow data;

a processor configured to:

generate adjusted blood pressure data corresponding to a second physiological state, based on the acquired blood pressure data and the first physiological state;

generate adjusted flow data corresponding to the second physiological state, based on the acquired flow data and the first physiological state;

generate a microvascular resistance score, based on the adjusted blood pressure data, the adjusted flow data and the throughflow data; and an output configured to:

provide, through an electronic output signal, the microvascular resistance score for display on a display module of an electronic computing device comprising the data processing device, for a user of the electronic computing device to evaluate perfusion of the myocardial tissue.

14. A computer program product comprising instructions which, when the program is executed by a computer, cause the computer to carry out a method of determining a microvascular resistance score, the method comprising:

obtaining acquired blood pressure data of a cardiac vessel supplying blood to myocardial tissue of a mammal, said acquired blood pressure data being acquired while the mammal is in a first physiological state;

obtaining acquired flow data of the blood in the cardiac vessel, said acquired flow data being acquired while the mammal is in the first physiological state;

obtaining throughflow data indicative of a geometry of the cardiac vessel, said throughflow data being acquired by:

measuring a length of the cardiac vessel from a proximal point to a distal point, measuring a transit time of the blood from the proximal point to the distal point, and dividing the length by the transit time to calculate the throughflow data;

generating adjusted blood pressure data corresponding to a second physiological state, based on the acquired blood pressure data and the first physiological state;

generating adjusted flow data corresponding to the second physiological state, based on the acquired flow data and the first physiological state;

generating the microvascular resistance score, based on the adjusted blood pressure data, the adjusted flow data and the throughflow data; and providing, through an electronic output signal, the microvascular resistance score for display on a display module of an electronic computing device, for a user of the electronic computing device to evaluate perfusion of the myocardial tissue.

15. A non-transitory computer readable medium comprising instructions which, when executed by a computer, cause the computer to carry out a method of determining a microvascular resistance score, the method comprising:

obtaining acquired blood pressure data of a cardiac vessel supplying blood to myocardial tissue of a mammal, said blood pressure data being acquired while the mammal is in a first physiological state;

obtaining acquired flow data of the blood in the cardiac vessel, said acquired flow data being acquired while the mammal is in the first physiological state;

obtaining throughflow data indicative of a geometry of the cardiac vessel, said throughflow data being acquired by:

measuring a length of the cardiac vessel from a proximal point to a distal point, measuring a transit time of the blood from the proximal point to the distal point, and dividing the length by the transit time to calculate the throughflow data;

generating adjusted blood pressure data corresponding to a second physiological state, based on the acquired blood pressure data and the first physiological state;

generating adjusted flow data corresponding to the second physiological state, based on the acquired flow data and the first physiological state;

generating the microvascular resistance score, based on the adjusted blood pressure data, the adjusted flow data and the throughflow data; and providing, through an electronic output signal, the microvascular resistance score for display on a display module of an electronic computing device, for a user of the electronic computing device to evaluate perfusion of the myocardial tissue.

* * * * *